United States Patent [19]

Hermann et al.

[11] Patent Number: 4,775,714

[45] Date of Patent: Oct. 4, 1988

[54] METHOD FOR PRODUCING HIGHLY-ACTIVE BIOLOGICALLY ACTIVE COMPOUNDS IMMOBILIZED ON A CARRIER

[75] Inventors: Peter Hermann, Halle/S.; Jiri Coupek, Prague; Kornelia Smalla, Magdeburg; Ingo Willhardt, Halle-Neustadt; Jaroslava Turkova, Cesky Brod, all of Czechoslovakia

[73] Assignee: Laboratorni pristroje, koncernovy podnik, Prague, Czechoslovakia

[21] Appl. No.: 807,339

[22] Filed: Dec. 10, 1985

[30] Foreign Application Priority Data

Dec. 11, 1984 [CS] Czechoslovakia ............... 9621-84

[51] Int. Cl.⁴ .................. C08H 89/00; C08H 1/00; C07G 7/00
[52] U.S. Cl. .................. 525/54.1; 530/402; 530/403; 530/811; 530/812
[58] Field of Search ............ 525/54.1; 530/402, 403, 530/811, 812

[56] References Cited

U.S. PATENT DOCUMENTS

| | | | |
|---|---|---|---|
| 4,104,363 | 8/1978 | Vozka et al. | 423/338 |
| 4,440,903 | 4/1984 | Golstein et al. | 525/54.1 |
| 4,511,694 | 3/1985 | Krämer et al. | 525/54.1 |
| 4,563,490 | 1/1986 | Stol et al. | 524/24 |

OTHER PUBLICATIONS

Smalla et al., "Influence of Salts on the Covalent Immobilization of Proteins to Modified Copolymers of 2-Hydroxyethyl Methacrylate with Ethylene Dimethaerylate", *Biochimica et Biophysiea Acta* (Manuscript 1981).

*Primary Examiner*—Delbert R. Phillips
*Assistant Examiner*—Nathan M. Nutter
*Attorney, Agent, or Firm*—Klein & Vibber

[57] ABSTRACT

A two-step process of immobilization of biologically efficient compounds is disclosed, in which the biologically efficient compounds are bonded from an aqueous solution by a hydrolytically stable linkage to a macroporous polymeric carrier containing reactive functional groups. In the first step, a hydrophobic adsorption occurs of the biologically efficient compounds on a macroporous matrix of the carrier, and an increase of their concentration on the solid surface. In the second step, the reaction takes place with the reactive functional groups of the carrier, and a covalent linkage is formed. The hydrophobic adsorption of compounds determined for immobilization is achieved by the addition of inorganic salts in a concentration from 0.5 to 3.0 mol/l. The invention can be utilized in the preparation of enzymatic catalysts for transformations of compounds and in the preparation of specific sorbents for both analytical and preparative affinity chromatography. These methods are employed in the fields of biotechnology, chemical and clinical analysis, food industry, pharmacology and clinical therapy.

10 Claims, No Drawings

METHOD FOR PRODUCING HIGHLY-ACTIVE BIOLOGICALLY ACTIVE COMPOUNDS IMMOBILIZED ON A CARRIER

BACKGROUND OF THE INVENTION

The invention pertains to a universal method for producing highly-active biologically active compounds in general, and, more particularly, to do so by immobilization with a covalent linkage on macroporous polymeric carriers in the presence of higher concentrations of inorganic salts.

Research and application of immobilized, biologically active compounds represents today an extensive field involving both development and application projects of considerable practical importance.

The preparation and application of insoluble enzymes by bonding a soluble enzyme to a carrier enables one to use the catalyst system repeatedly in a batch or through-flow arrangement of reaction in which the insoluble enzyme has the role of the specific heterogeneous catalyst. Such arrangement of the catalytic enzymatic reaction facilitates the subsequent separation of the enzyme from substrate and reaction products, and lowers the cost while enabling one to automate the process in multiple or continuous performance.

The rate of enzymatically catalyzed reaction, insofar as the interaction of a substrate with the covalently immobilized enzyme, depends also on the character of linkage enzyme-carrier, i.e. on physical and chemical properties of the carrier (the size and distribution of pores, hydrophilicity of surface, etc.). Hydrodynamic parameters of the system, the flow rate of substrate, temperature, and others also significantly influence the final yield of reaction. The detailed knowledge of the factors affecting enzymatically catalyzed reactions utilizing the immobilized enzymes was obtained also by investigations of the processes on a preparative scale (penicilinacylase) (I. CHIBATA, Immobilized Enzymes, J. Wiley and sons, New York 1970).

Immobilized, biologically active compounds have found a very broad application in affinity chromatography. This method employs the capacity of numerous biologically active compounds to form sorption complexes with other compounds, while the character of interaction is very specific and reversible. If one of the components of a sorption complex is bonded to a solid carrier, only such compounds that are noted for their specific affinity to the bonded compound are selectively adsorbed from solution under suitable conditions. The sorption complex may be easily separated from other components in solution by means of the carrier. Dissociation of the sorption complex and separation of the soluble component from the component which remains chemically bonded to the carrier occur by change of conditions (pH, ionic strength, temperature, addition of competitive sorbates, and the like). This procedure finds use in the isolation and purification of enzymes, enzyme inhibitors, antidotes, antigens, soluble proteins, etc. Immobilization of bioactive compounds is advantageously used in biochemical analysis in the application of radioactive-labelled compounds or in optical labelling.

Numerous materials are employed as carriers of biologically active compounds, for example, porous glass, silica gel, activated carbon, cellulose and its derivatives, starch, agarose, cross-linked polydextrans, synthetic polymers and copolymers such as polyacrylamide, polystyrene, polyamides, poly(maleic anhydride), polyacrylates, polymethacrylates, etc. Some types are unsuitable because they carry ionogenic functional groups; others are noted for their strong non-specific sorption properties for proteins. Other types have insufficient mechanical, hydrolytical, microbial or thermal stability or unsuitable pore size distribution. These features considerably narrow their region of application. Homogeneous hydrophilic carriers of polysaccharide type mainly must not dry out, a fact which makes their storage and transportation difficult.

Most of the above-mentioned shortcomings are overcome in carriers prepared by copolymerization of 2-hydroxyalkyl methacrylates with alkylene dimethacrylates, which are activated by substitution on the hydroxyl group for the purpose of immobilization reaction (J. Coupek, J. Turkova, O. Hubalkova, M. Krivakova; Czechoslovak Pat. No. 167,530).

Further detailed studies concerning the mechanisms of immobilization of biologically active compounds reveal that the covalent linkage has to be as stable as possible towards hydrolysis, which cannot be satisfied, for example, by activation with cyanogen bromide or by amide, sulfide, ester or other bonding groups. Immobilization proved most suitable utilizing reactive epoxide groups according to the following scheme:

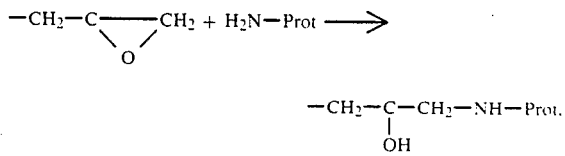

where Prot means the residue of protein.

Experiments with immobilization on the copolymer of glycidyl methacrylate with ethylene dimethacrylate (J. Turkova, K. Blaha, M. Malanikova, D. Vajenerova, F. Svec and J. Kalal; Biochem. Biophys. Acts 5424 (1978) (62) revealed that the reactive glycidyl methacrylate groups enclosed in a strongly cross-linked matrix of copolymer cannot be wholly employed for immobilization, and that their subsequent deactivation is difficult. Therefore, a macroporous copolymer of 2-hydroxyethyl methacrylate with ethylene dimethacrylate was advantageously used as a carrier which was activated with epichlorohydrine and contained epoxypropyl functional groups only on the inner surfaces of porous particles (J. Turkova, K., J. Horacek, J. Vagener, A. Frydrychove and J. Coupek; J. Chromatogr. 215 (1981) (165–179) and on the surface of particles.

However, the yield of immobilized activity was rather low in some cases of direct bonding of protein on the epoxypropyl derivative of the hydroxyethyl methacrylate copolymer. This shortcoming, which occurs also in several other known activations of synthetic polymeric carriers, is overcome by the subject of this invention.

SUMMARY OF THE INVENTION

The present invention is directed to a method for producing highly-active immobilized, biologically active compounds for chemical transformation of compounds by enzymatic catalysis and covalent linking of biologically efficient compounds to a macroporous polymeric carrier, wherein the biologically active compounds are linked on an activated carrier in the presence of inorganic salts added in a concentration from 0.5 to 3.0 mole/liter. The concentration of inorganic salts in the bonding reaction causes reduction or elimination of a solvation envelope of protein molecules. In the first step, a hydrophobic adsorption of biologically active compounds on the carrier takes place, while in the second step the biologically active compounds react with functional groups of the carrier, resulting in to the covalent linkage.

The macroporous polymeric carriers are selected from the groups comprising synthetic copolymers of hydroxyalkyl methacrylates ($C_2$ to $C_6$ alkyl) with alkylene dimethacrylate ($C_2$ to $C_4$ alkylene), copolymers of styrene with divinylbenzene or alkylene dimethacrylate ($C_2$ to $C_4$ alkylene), copolymers of glycidyl methacrylate with ethylene dimethacrylate, porous glass, and silica gel.

The polymeric carrier has to be activated prior to the immobilization reaction. Reactive functional groups are selected from the group comprising epoxides, aldehydes, primary or secondary amines, carboxyls and thiols. The macroporous polymeric carrier advantageously has a rigid structure and spherical shape. To confirm the effect of the invention, they were chosen from the compounds comprised in the group of enzymes, enzyme inhibitors, and also immunoactive proteins.

Salts, the presence of which in bonding of bioactive compounds substantially increases the yield of bonded protein and the yield of activity, are selected from the group comprising ammonium and sodium sulfates and phosphates. Reaction temperature is selected according to the reactivity of functional groups of the carrier and the bioactive compound determined for immobilization, and lies in the interval −5 degrees C. to 30 degrees C. The reaction proceeds at pH 3–10 for 0.5 to 40 hours.

The method for immobilization of biologically active compounds in the presence of higher concentrations of inorganic salts according to the present invention is highly universal. Its mechanism has been studied insofar as details, and confirmed with numerous biologically active compounds of various nature. The subject of the invention is further elucidated and substantiated in several examples, which, however, do not limit its scope by any means.

DESCRIPTION OF THE PREFERRED EMBODIMENTS

Example 1

Enzyme aminoacylase (3.5.1.14.) (10 mg) is dissolved in 5 ml of 0.2M solution of phosphate buffer (pH 7). Ammonium sulfate is added, after the dissolution of protein is completed, in such a manner that the final concentration of salt amounts to 1.75 mol/l of solution. Then, 100 mg of copolymer of 2-hydroxyethyl methacrylate with ethylene dimethacrylate (SEPARON 1000; exclusion limit $E_{max}=2\times 10^6$ Dalton, particle size 40–80 μm, capacity of surface-bonded epoxide groups 1.77 mmol/g) is added. To speed up penetration of the solution into the macroporous structure of the carrier, the suspension is kept under vacuum of a water-jet pump (15 mm Hg column) for 5 minutes. Immobilization of acylase is carried out for 30 hours at 4 degrees C. under moderate shaking of the suspension. After complete immobilization, the carrier is washed with a buffer solution (phosphate, pH 7) and with 1M NaCl solution. The content of bonded protein and its enzymatic activity are then determined. The yield of bonded activity is 10% with respect to the employed protein, and 20% with respect to the bonded protein.

Example 2

The reaction is carried out in a similar manner as in example 1, with the distinction that it proceeds in the presence of an optimum amount of ammonium monohydrogensulfate (1.5 mol/l). The yields of activity are the same as in Example 1.

Example 3

Enzyme thermitase (3.4.21.14.) (1 mg) is dissolved in 5 ml of 0.2M phosphate buffer with pH 8.0. A solution of ammonium sulfate is added in such a manner that the total concentration of salt is 2.0 mol/l. Similar as to Example 1, 100 mg of a carrier is added, which contains epoxide groups (1.77 mmol/g) on the copolymer of 2-hydroxyethyl methacrylate with ethylene dimethacrylate, and the suspension is subjected to vacuum of a water-jet pump for 5 minutes. The reaction takes 40 hours at 20 degrees C. under moderate shaking in this case. The yield of activity is 10%.

Example 4

The reaction is carried out analogous to example 3, with the distinction that the optimum concentration of added salt (sodium sulfate) is 1.25 mol/l. The reaction conditions and the yield of activity of the immobilized enzyme are the same as in Example 3.

Example 5

100 mg of an activated carrier with particle size 100–200 μm are added to 1 mg of enzyme penicilinacylase (3.5.1.11.) in 5 ml of phosphate buffer (0.2M, pH 8) and then, stepwise, a solution of ammonium sulfate, in such a manner that the final concentration of salt amounts to 2.5 mol/l. The reaction is carried out at 40 degrees C. for 40 hours under moderate shaking. The reaction mixture is worked out in the same way as in Example 1. The yield of activity is 45%.

Example 6

100 mg of a copolymer of 2-hydroxypropyl methacrylate cross-linked with butylene dimethacrylate (exclusion limit $8\times 10^5$ Dalton; particle size 80–100 μm) activated with epoxy groups (capacity 1.25 mmol/g) are added to 5 mg of enzyme elastase (3.4.21.36.) in 5 ml of 0.2M phosphate buffer of pH 8.0. A solution of sodium hydrogensulfate is added, up to a final concentration of 1.5 mol/l. The reaction takes 20 hours at 4 degrees C. under moderate shaking. The yield of activity is 17%.

Example 7

Cystathion-β-synthetase (4.2.1.22.) (10 mg) is dissolved in 5 ml of 0.2M TRIS-HCl buffer solution at pH 8.7. 100 mg of a carrier having the same composition as in Example 1 is added, followed by the solution of ammonium sulfate up to its optimum concentration of 2.5 mol/l. The reaction takes 40 hours at −4 degrees C. The reaction mixture is worked out according to Example 1. The yield of activity is 35%.

Example 8

100 mg of a carrier prepared by copolymerization of glycidyl methacrylate with ethylene dimethacrylate 1:2 (exclusion limit $1\times 10^6$ Dalton, particle size 100–200 μm) are added to 1 mg of carboxypeptidase A (3.4.17.1)

dissolved in 5 ml of 0.2M phosphate buffer. The bonding reaction is carried out in the presence of 2.0 mol/l of ammonium sulfate at 4 degrees C. for 20 hours. The product is worked out according to Example 1 and the yield of activity related to the protein added is determined to be 11.5%.

Example 9

Anti-cathepsin D-IgG (3 mg) is dissolved in 5 ml of 0.2M phosphate buffer of pH 8.0 and bonded to 100 mg of carrier, which is the same as in Example 1, in the presence of 1.5 mol/l ammonium sulfate for 24 hours at 25 degrees C. under moderate shaking. After the reaction is completed, the carrier with the bonded protein is isolated by filtration, washed with the above-mentioned buffer solution, packed into a column and tested for application in the affinity chromatography of Cathepsin D-IgG.

Example 10

The carrier according to Example 1 (250 mg) is allowed to react at 50 degrees C. with 1 g of mexamethylenediamine in 5 ml of water under moderate stirring for 3 hours. The reaction mixture is then washed with water. The wet sorbent, after washing, is dispersed in 2 ml of 5% aqueous solution of glutaraldehyde, shaken for 20 hours and washed with water until the reaction with diphenylhydrazine is negative. The wet, activated carrier is then mixed with a solution of trypsin-inhibitor isolated from potatoes (1 mg/ml), 2 ml of $1.25Na_2SO_4$ is added, the reaction mixture is moderately shaken for 5 hours at 25 degrees C. and the carrier is then filtered and washed with water. The immobilized inhibitor is used for the affinity chromatography of trypsin.

Example 11

Chymotrypsin (3.4.21.1.) (10 mg) is dissolved in 5 ml of 0.2M phosphate buffer solution of pH 8 and 100 mg of carrier based on the epoxypropyl derivative of silica gel (exclusion limit $5 \times 10^5$ Dalton, capacity 0.5 mmol/g) is added to the mixture. Ammonium sulfate (2.5 mol/l) is added, and the bonding reaction is carried out for 20 hours at 30 degrees C. After washing according to Example 1, the yield of activity of the bonded chymotrypsin is determined to be 8.5%.

Example 12

This experiment is carried out analogous to Example 11, with the distinction that porous glass with a mean pore diameter of 500 Å is employed as the carrier. The carrier is activated by reaction with triethoxyepoxypropylsilane. The yield of activity of the bonded chymotrypsin is 9.7%.

Example 13

Trypsin (3.4.21.4.) (10 mg) is dissolved in 5 ml of 0.2M phosphate buffer with pH 8, and then 100 mg of carrier according to example 1 is added. The reaction takes 20 hours at the ammonium sulfate concentration of 2.5 mol/l and at ambient temperature.

Example 14

Pepsin (3.4.23.1.) (10 mg) is mixed into 5 ml of 0.1M acetate buffer of pH 4.0 with 100 mg of carrier in a manner similar to that of example 1. The reaction proceeds for 24 hours at the optimum ammonium sulfate concentration of 1.25 mol/l and a temperature of 25 degrees C. After washing according to Example 1, the yield of immobilized activity is found to be 15%.

Example 15

100 g of epoxy-activated carrier according to Example 1 are added to 10 mg of insulin in 5 ml of 0.05M phosphate buffer of pH 8. The bonding reaction is carried out in the presence of 1.75 mol/l of sodium monohydrogenphosphate at 25 degrees C. for 50 hours. The bonded insulin is employed for the affinity chromatography of antidotes against insulin from an antiinsulin serum in 0.1M sodium barbiturate of pH 8.8, which contains 3% of albumin. The antidotes are desorbed with 3M aqueous HCl.

We claim:

1. Method for producing highly active immobilized, biologically active compounds useful for chemical transformation of compounds by enzymatic catalysis and for preparative and analytical separation techniques, by means of a hydrolytically stable covalent linking of biologically active compounds to macroporous polymeric carriers, comprising linking said biologically active compounds to an activated macroporous polymeric carrier in the presence of solutions of inorganic salts added in a concentration from 0.5 to 3 mol/l, the given concentration of inorganic salt present in the bonding reaction causing a two-step reaction, whereby a hydrophobic adsorption of the biologically active compound on the carrier occurs in the first step and then, in the second step, the biologically active compounds react with the carrier, resulting in a covalent linkage.

2. The method according to claim 1, wherein the macroporous polymeric carriers are selected from the group consisting of copolymers of hydroxyalkyl methacrylates ($C_2$ to $C_6$-alkyl) with alkylene dimethacrylate ($C_2$ to $C_4$-alkylene), copolymers of styrene with divinylbenzene or alkylene dimethacrylate ($C_2$ to $C_4$-alkylene), copolymers of glycidyl methacrylate with alkylene dimethacrylate ($C_2$ to $C_4$-alkylene), porous glass, and silica gel.

3. The method according to claim 1, wherein the macroporous polymeric carrier contains functional groups selected from the group consisting of epoxides, aldehydes, primary and secondary amines, carboxyls and thiols.

4. The method according to claimn 1, wherein the macroporous polymeric carrier possesses a rigid structure and spherical form.

5. The method according to claim 1, wherein the covalently bonded biologically active compounds are selected from the group consisting of enzymes, enzyme inhibitors and immunoactive proteins.

6. The method according to claim 1, wherein the salts are selected from the group consisting of sodium phosphates, ammonium phosphates, sodium sulfates and ammonium sulfates.

7. The method according to claim 1, wherein the bonding reaction is carried out in the temperature range from −5 degrees C. to 30 degrees C., at a pH of 3 to 10, and for a period of 0.5 to 50 hours.

8. A highly-active immobilized biologically active compound comprising a biologically active compound covalently linked in a hydrolytically stable manner to an activated macroporous polymeric carrier in the presence of solutions of inorganic salts in a concentration from 0.5 to 3 mol/l, the given concentration of inorganic salt present in the bonding reaction causing a two-step reaction, whereby a hydrophobic adsorption of the biologically active compound on the carrier occurs in the first step and then, in the second step, the biologically active compound reacts with the carrier, resulting in a covalent linkage between the biologically active compound and the carrier.

9. A method for producing highly active immobilized, biologically active compounds useful for chemical transformation of compounds by enzymatic catalysis and for preparative and analytical separation techniques, by means of a hydrolytically stable covalent linking of biologically active compounds having a functional group selected from the group consisting of a primary amine and hydroxy group, to macroporous polymeric carriers, comprising linking said biologically active compounds to an activated macroporous polymeric carrier in the presence of solutions of inorganic salts added in a concentration from 0.5 to 3 mol/l, the given concentration of inorganic salt present in the bonding reaction causing a two-step reaction, whereby a hydrophobic adsorption of the biologically active compound on the carrier occurs in the first step and then, in the second step, the biologically active compounds react with the carrier, resulting in immobilization via a covalent linkage.

10. The method according to claim 9, wherein the activated macroporous polymeric carrier contains functional groups selected from the group consisting of epoxides, aldehydes, primary and secondary amines, carboxyls and thiols.

* * * * *